United States Patent
Kondrk et al.

(10) Patent No.: US 11,662,109 B2
(45) Date of Patent: May 30, 2023

(54) ENCLOSURE FOR GAS DETECTOR

(71) Applicant: Carrier Corporation, Palm Beach Gardens, FL (US)

(72) Inventors: Jason R. Kondrk, Clay, NY (US); Linus Hjern, Hudiksvall (SE); Joakim Enerud, Hudiksvall (SE); Yuji Goda, Hudiksvall (SE); Martin Lownertz, Bjuraker (SE); Mats Olsson, Bollnas (SE)

(73) Assignee: CARRIER CORPORATION, Palm Beach Gardens, FL (US)

(*) Notice: Subject to any disclaimer, the term of this patent is extended or adjusted under 35 U.S.C. 154(b) by 299 days.

(21) Appl. No.: 16/894,071

(22) Filed: Jun. 5, 2020

(65) Prior Publication Data
US 2020/0386431 A1    Dec. 10, 2020

Related U.S. Application Data

(60) Provisional application No. 62/857,635, filed on Jun. 5, 2019.

(51) Int. Cl.
| | |
|---|---|
| *F24F 11/36* | (2018.01) |
| *F25B 49/00* | (2006.01) |
| *H05K 1/18* | (2006.01) |
| *G01N 21/88* | (2006.01) |
| *G01N 33/00* | (2006.01) |
| *F25D 11/00* | (2006.01) |

(52) U.S. Cl.
CPC ............ *F24F 11/36* (2018.01); *F25B 49/005* (2013.01); *G01N 21/88* (2013.01); *G01N 33/0009* (2013.01); *H05K 1/181* (2013.01); *F25B 2500/222* (2013.01); *F25D 11/003* (2013.01); *G01N 2201/022* (2013.01); *H05K 2201/10151* (2013.01)

(58) Field of Classification Search
CPC ... F24F 11/36; F25B 49/005; F25B 2500/222; F25D 11/003; H05K 1/181; H05K 2201/10151
See application file for complete search history.

(56) References Cited

U.S. PATENT DOCUMENTS

| | | | |
|---|---|---|---|
| 6,073,455 A | 6/2000 | Tachigori et al. | |
| 6,518,574 B1 | 2/2003 | Castleman | |
| 6,644,047 B2 | 11/2003 | Taira et al. | |

(Continued)

FOREIGN PATENT DOCUMENTS

| | | |
|---|---|---|
| CN | 201110830 Y | 9/2008 |
| CN | 105181621 A | 12/2015 |

(Continued)

OTHER PUBLICATIONS

JP 3349783 (English translation) (Year: 1993).*

(Continued)

*Primary Examiner* — Jonathan Bradford
(74) *Attorney, Agent, or Firm* — Cantor Colburn LLP

(57) ABSTRACT

A gas detector is provided and includes a gas detector element, electronics to interface with the gas detector element and an enclosure configured to expose the gas detector element to an exterior and to form an electronics housing area in which the electronics are disposed whereby the electronics are isolated from the exterior.

8 Claims, 4 Drawing Sheets

(56) References Cited

U.S. PATENT DOCUMENTS

| | | | |
|---|---|---|---|
| 6,921,899 B2 | 7/2005 | Martin | |
| 6,943,885 B2 | 9/2005 | Martin | |
| 7,176,578 B2 | 2/2007 | Martin et al. | |
| 7,564,558 B2 | 7/2009 | Martin | |
| 8,257,655 B2 | 9/2012 | Martin | |
| 8,368,895 B2 | 2/2013 | Martin | |
| 8,796,629 B2 | 8/2014 | Martin | |
| 9,001,331 B2 | 4/2015 | Martin et al. | |
| 9,054,224 B2 | 6/2015 | Braun et al. | |
| 9,448,159 B2 | 9/2016 | Martin | |
| 9,625,195 B2 | 4/2017 | Hiraki et al. | |
| 9,879,871 B2 | 1/2018 | Goel et al. | |
| 10,060,645 B2 | 8/2018 | Yamaguchi et al. | |
| 10,209,180 B2 | 2/2019 | Gylfason et al. | |
| 10,229,549 B2 | 3/2019 | Gester et al. | |
| 2011/0235042 A1 | 9/2011 | Martin et al. | |
| 2017/0370605 A1 | 12/2017 | Makino et al. | |
| 2018/0045424 A1 | 2/2018 | Yajima et al. | |
| 2018/0259235 A1 | 9/2018 | Delgoshaei | |
| 2018/0280746 A1 | 10/2018 | Damazo et al. | |

FOREIGN PATENT DOCUMENTS

| | | | |
|---|---|---|---|
| EP | 1956363 A1 | | 8/2008 |
| EP | 2589900 B1 | | 5/2013 |
| EP | 3150943 A1 | | 4/2017 |
| JP | 11304706 A | | 11/1999 |
| JP | 2004177150 A | * | 6/2004 |
| JP | 2016070568 A | | 5/2016 |
| JP | 201219276 A | | 12/2017 |
| WO | 2005054827 A1 | | 6/2005 |
| WO | 201529094 A1 | | 3/2015 |
| WO | 2018147428 A1 | | 8/2018 |
| WO | 2018154347 A1 | | 8/2018 |
| WO | 2018187450 A1 | | 10/2018 |
| WO | 2019013049 A1 | | 1/2019 |
| WO | 2019013135 A1 | | 1/2019 |

OTHER PUBLICATIONS

European Search report Application No. EP20275110; dated Oct. 16, 2020; pp. 6.

CO2 metering with Senseair S8—YouTube; downloaded Mar. 9, 2020; pp. 1.

http://www.operadetectors.com/media/ecommerce_product.pdf/en-CA/60xx%20Data%20Sheet%20v2.0%20English%20Web.pdf; downloaded Jan. 20, 2020; pp. 4.

https://www.youtube.com/watch?v=vvPJdH4Pu-0; downloaded Mar. 9, 2020; pp. 1.

IEC; IEC 60079-29-1; International Standard; Explosive Atmospheres—Part 29-1: Gas Detectors—Performance Requirements of Detectors for Flammable Gases Edtion 2.0; Jul. 2016; pp. 104.

Lu He, et al.: Exploring the Business Opportunity for the Chinese Market Entry for a European Component Producer: Chalmers University of Technology: Report No. E2011:098; Gothenburg, Sweden, 2011: pp. 74.

Mark: "Datasheet and Manual Sense Air S8"; Dated Feb. 9, 2016; pp. 9.

Vertrieb Hoppe: "Sense Air S8 Driesen Kem GmBH 13"; Dated Jul. 2, 2012; pp. 9.

www.CO2meter.com; downloaded Jan. 20, 2020; pp. 2.

* cited by examiner

ENCLOSURE FOR GAS DETECTOR

CROSS-REFERENCE TO RELATED APPLICATIONS

This application claims the benefit of Provisional Application No. 62/857,635 filed Jun. 5, 2019, the disclosure of which is incorporated herein by reference in its entirety.

BACKGROUND

The following description relates to gas detector enclosures and, more specifically, to an enclosure for a non-dispersive infrared (NDIR) gas detector for low global warning potential (GWP) refrigerants.

A typical refrigerated cargo container, such as those utilized to transport cargo via sea, rail or road, is a container modified to include a refrigeration unit located at one end of the container. The refrigeration unit includes a compressor, condenser, expansion valve and evaporator. A volume of refrigerant circulates throughout the refrigeration unit, and one or more evaporator fans of the refrigeration unit blow a flow of supply air across the evaporator thereby cooling the supply air and forcing it out into the container.

In those cases in which the refrigeration unit uses a refrigeration cycle to cool the supply air, a portion of the volume of the refrigerant can may leak inside the conditioned space. As the refrigerant can be a low GWP refrigerant, for example, which is mildly flammable, a leak of the refrigerant inside the conditioned space can pose a danger to the refrigerated cargo and to personnel handling the refrigerated cargo container.

Therefore, gas detectors are often provided in refrigerated cargo containers or the refrigeration unit in order to sense gas being present due to a leak. Such gas detectors can include non-dispersive infrared (NDIR) technology and are used to determine concentrations of particular gases in a given atmosphere. It is typically the case that response times for these types of sensing elements are the duration of time required for the sensing elements to accurately respond once a gas is introduced and it is understood that the response times can be delayed if environmental packaging of electronics can trap gas or uncontaminated air during gaseous introduction to the sensing elements.

BRIEF DESCRIPTION

According to an aspect of the disclosure, a gas detector is provided and includes a gas detector element, electronics to interface with the gas detector element and an enclosure configured to expose the gas detector element to an exterior and to form an electronics housing area in which the electronics are disposed whereby the electronics are isolated from the exterior.

In accordance with additional or alternative embodiments, the gas detector further includes a printed circuit board (PCB) and the PCB includes a first side on which the gas detector element is disposable and a second side opposite the first side on which the gas detector electronics are disposable.

In accordance with additional or alternative embodiments, the PCB includes a solid, unitary body configured to impede fluid flow from the exterior to the electronics housing area.

In accordance with additional or alternative embodiments, the enclosure includes a body and a cover with the PCB being affixable to the body and the cover being affixable to the body over the PCB.

In accordance with additional or alternative embodiments, the cover defines an aperture through which the gas detector element is exposed to the exterior and the body cooperates with the PCB to form the electronics housing area in which the gas detector electronics are disposable.

In accordance with additional or alternative embodiments, the cover includes a cover portion and a spacer portion interposed between the PCB and the cover portion.

In accordance with additional or alternative embodiments, the spacer portion is thicker than the gas detector element.

In accordance with additional or alternative embodiments, the spacer portion defines an opening to accommodate the gas detector element and includes a seal at the opening.

In accordance with additional or alternative embodiments, the gas detector element and the gas detector electronics are disposable on a same side of the PCB.

In accordance with additional or alternative embodiments, the PCB defines a PCB aperture through which the gas detector element is exposable to the exterior and the PCB includes a solid, unitary body surrounding the PCB aperture and configured to impede fluid flow from the exterior to the electronics housing area.

According to another aspect of the disclosure, a refrigeration system is provided and is configured to condition an interior volume of a conditioned space. The refrigeration system includes the gas detector, which is deployed within the interior volume.

According to another aspect of the disclosure, a gas detector is provided and includes a printed circuit board (PCB) on which a gas detector element and electronics to interface with the gas detector element are disposable and an enclosure. The enclosure includes a body and a cover which are attachable together to substantially surround the PCB. The cover defines an aperture through which the gas detector element at the first side of the PCB is exposed to an exterior. The body defines, in cooperation with the PCB, an electronics housing area in which the electronics at the second side of the PCB are disposable. The electronics housing area is isolated from the exterior.

In accordance with additional or alternative embodiments, the PCB includes a solid, unitary body configured to impede fluid flow from the exterior to the electronics housing area.

In accordance with additional or alternative embodiments, the PCB is affixable to the body and the cover is affixable to the body over the PCB.

In accordance with additional or alternative embodiments, the cover includes a cover portion and a spacer portion interposed between the PCB and the cover portion. The spacer portion is thicker than the gas detector element, defines an opening to accommodate the gas detector element and includes a seal at the opening.

In accordance with additional or alternative embodiments, the gas detector element and the electronics are disposable on a same side of the PCB.

According to another aspect of the disclosure, a gas detector is provided and includes a printed circuit board (PCB) having a first side on which a gas detector element is disposable and a second side opposite the first side on which electronics to interface with the gas detector element are disposable and an enclosure. The enclosure includes a body and a cover which are attachable together to substantially surround the PCB. The cover defines an aperture through which the gas detector element at the first side of the PCB is exposed to an exterior. The body defines, in cooperation with the PCB, an electronics housing area in which the electronics at the second side of the PCB are disposable. The electronics housing area is isolated from the exterior.

In accordance with additional or alternative embodiments, the PCB includes a solid, unitary body configured to impede fluid flow from the exterior to the electronics housing area.

In accordance with additional or alternative embodiments, the PCB is affixable to the body and the cover is affixable to the body over the PCB.

In accordance with additional or alternative embodiments, the cover includes a cover portion and a spacer portion interposed between the first side of the PCB and the cover portion. The spacer portion is thicker than the gas detector element, defines an opening to accommodate the gas detector element and includes a seal at the opening.

These and other advantages and features will become more apparent from the following description taken in conjunction with the drawings.

BRIEF DESCRIPTION OF THE DRAWINGS

The subject matter, which is regarded as the disclosure, is particularly pointed out and distinctly claimed in the claims at the conclusion of the specification. The foregoing and other features and advantages of the disclosure are apparent from the following detailed description taken in conjunction with the accompanying drawings in which:

These and other advantages and features will become more apparent from the following description taken in conjunction with the drawings.

DETAILED DESCRIPTION

As will be described below, an enclosure design is provided that isolates a gas detector diffusion membrane from electrical components required to be protected within the enclosure. The enclosure design eliminates open spaces that can hold air and prevent gas introduction to the sensor, or that can hold flammable gas and prevent the sensor from recognizing a safe environment. The enclosure design can significantly reduce delays in response times (e.g., from about 20 minutes to 1 minute) and can allow an associated refrigeration system to create a safety warning or initiate mitigation strategies at faster rates. The enclosure design can also allow the associated refrigeration system to reactivate when a surrounding environment is deemed safe.

Figure 1:
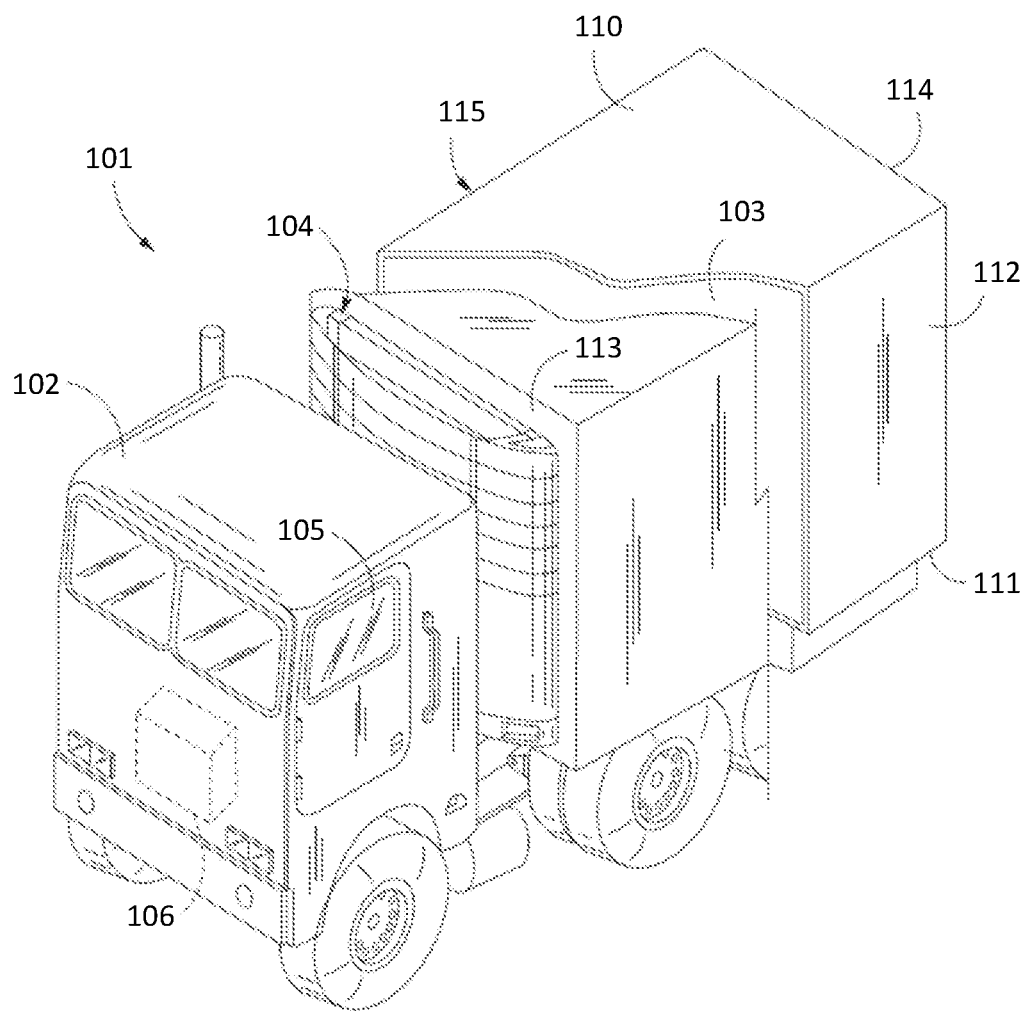
FIG. 1 is a perspective view of a transport vehicle in accordance with embodiments.

With reference to FIG. 1, a transport system 101 is illustrated and includes a tractor or vehicle 102, a conditioned space 103 that is pulled by the vehicle 102 and a refrigeration system 104 that conditions the air within the conditioned space 103.

While the transport system 101 is described herein as being a conditioned space 103 pulled by vehicle 102, it is to be understood that embodiments exist in which the conditioned space 103 is shipped by rail, sea or air or may be provided within any suitable container where the vehicle 102 is a truck, train, boat, airplane, helicopter, etc.

The vehicle 102 may include an operator's compartment or cab 105 and a vehicle motor 106. The vehicle 102 may be driven by a driver located within the cab, driven by a driver remotely, driven autonomously, driven semi-autonomously or any combination thereof. The vehicle motor 106 may be an electric or combustion engine powered by a combustible fuel. The vehicle motor 106 may also be part of the power train or drive system of a trailer system, thus the vehicle motor 106 is configured to propel the wheels of the vehicle 102 and/or the wheels of the conditioned space 103. The vehicle motor 106 may be mechanically connected to the wheels of the vehicle 102 and/or the wheels of the conditioned space 103.

The conditioned space 103 may be coupled to the vehicle 102 and is thus pulled or propelled to desired destinations. The conditioned space 102 may include a top wall 110, a bottom wall 111 opposed to and spaced from the top wall 110, two side walls 112 spaced from and opposed to one-another and opposing front and rear walls 113 and 114 with the front wall 113 being closest to the vehicle 102. The conditioned space 103 may further include doors (not shown) at the rear wall 114 or any other wall. The top, bottom, side and front and back walls 110, 111, 112 and 113 and 114 together define the boundaries of a refrigerated interior volume 115. The refrigeration system 104 is configured to condition the refrigerated interior volume 115.

Figure 2:
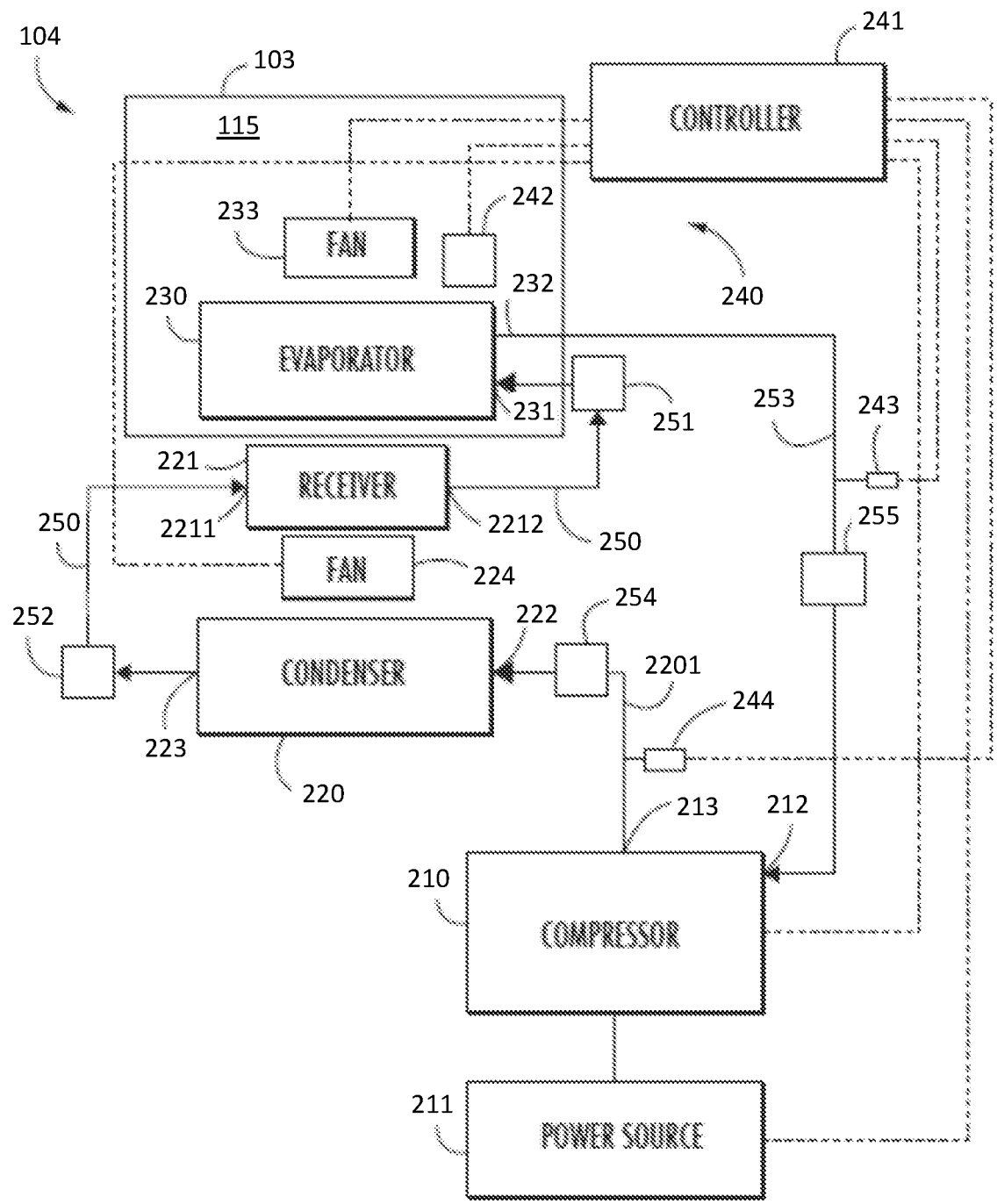
FIG. 2 is a schematic diagram of a refrigeration system of the transport vehicle of FIG. 1 in accordance with embodiments.

With reference to FIG. 2, the conditioned space 103 may be provided as an interior of a refrigerated trailer, a refrigerated truck, a refrigerated space or a refrigerated container with the refrigeration system 104 adapted to operate using a refrigerant such as a low GWP refrigerant such as A1, A2, A2L, A3, etc. In some cases, the refrigerant may leak into the refrigerated interior volume 115 and may present a hazard should the concentration of the leaked refrigerant within refrigerated interior volume 115 exceed a threshold level. The threshold level may be a lower flammability limit of the refrigerant.

An evaporator 230, a portion of a refrigerant line 253 proximate an evaporator outlet 232 and a portion of a refrigerant line 250 proximate an evaporator inlet 231 may be located within the refrigerated interior volume 115 of the conditioned space 103 and thus may be a potential source of a refrigerant leak.

The refrigeration system 104 may be a transport refrigeration system such as a transportation refrigeration unit (TRU). The refrigeration system 104 includes a compressor 210, a condenser 220, an evaporator 230 and a leak detection system 240 that includes a leak sensor 242, which is communicative with a controller 241. The leak detection system 240 is arranged to detect and mitigate the presence of refrigerant within the refrigerated interior volume 115.

The compressor 210 is powered by or driven by a power source 211. The compressor 210 receives refrigerant through a compressor inlet 212 from the evaporator 230 and discharges refrigerant through a compressor outlet 213 to the condenser 220 through a receiver 221. The condenser 220 receives a fluid flow of refrigerant from the compressor 210 through a condenser inlet 222 and discharges a fluid flow of refrigerant through a condenser outlet 223 to the receiver 221. The condenser inlet 222 is fluidly connected to the compressor outlet 213 through a refrigerant line 2201. A fan, such as a condenser fan 224, may be associated with and disposed proximate to the condenser 220.

The evaporator 230 is arranged to receive a fluid flow of refrigerant from the condenser 220 through an evaporator inlet 231 and is arranged to discharge a fluid flow of refrigerant to the compressor 210 through an evaporator outlet 232. The evaporator inlet 231 is fluidly connected to the condenser outlet 223 through the receiver 221 via a refrigerant line 250 through a first valve 251 and/or a second valve 252 that is disposed on an opposite side of the receiver 221 than the first valve 251. The evaporator outlet 232 is fluidly connected to the compressor inlet 212 through a refrigerant line 253. A fan such as an evaporator fan 233 may be associated with and disposed proximate to the evaporator 230.

The first valve 251 may be an expansion valve such as an electronic expansion valve, a movable valve or a thermal expansion valve. The first valve 251 is movable between an open position and a closed position to selectively inhibit and facilitate a fluid flow of refrigerant between the evaporator 230 and at least one of the condenser 220 and the receiver 221. The open position facilitates a fluid flow of refrigerant between the evaporator inlet 231 and the condenser outlet 223 through the receiver 221. The closed position inhibits a fluid flow of refrigerant between the evaporator inlet 231 and the condenser outlet 223 through the receiver 221 as well as inhibits a fluid flow of refrigerant between the receiver 221 and the evaporator inlet 231.

The receiver 221 is fluidly connected to the condenser 220 and the evaporator 230 and is arranged to receive and store refrigerant based on a position of at least one of the first valve 251 and/or the second valve 252. The receiver 221 is arranged to receive refrigerant from the condenser outlet 223 through a receiver inlet 2211 via the refrigerant line 250. In at least one embodiment, the second valve 252 is arranged to selectively facilitate a fluid flow between the condenser outlet 223 and the receiver inlet 2211. The second valve 252 may be a movable valve, a solenoid valve, a liquid service valve, a thermal expansion valve or an electronic expansion valve and is movable between open and closed positions to facilitate or impede a fluid flow of refrigerant between the condenser outlet 223 and the first receiver inlet 2211. The receiver 221 is arranged to discharge or provide a fluid flow of refrigerant through a receiver outlet 2212 to the evaporator inlet 231 via the first valve 251 through the refrigerant line 250.

A third valve 254 may be arranged to selectively facilitate a fluid flow between the compressor outlet 213 and the condenser inlet 222. The third valve 254 may be a movable valve, check valve, a liquid service valve, a thermal expansion valve, or an electronic expansion valve and is movable between open and closed positions to facilitate or impede a fluid flow of refrigerant between the compressor outlet 213 and the condenser inlet 222.

A fourth valve 255 may be arranged to selectively facilitate a fluid flow between the evaporator outlet 232 and the compressor inlet 212. The fourth valve 255 may be a movable valve, check valve, a liquid service valve, a thermal expansion valve, or an electronic expansion valve and is movable between open and closed positions to facilitate or impede a fluid flow of refrigerant between the evaporator outlet 232 and the compressor inlet 212.

The leak detection system 240 includes the leak sensor 242, which is communicative with the controller 241. The leak sensor 242 may be disposed and configured to detect the presence, or a selected amount or concentration, of refrigerant and thus to detect a refrigerant leak within the refrigerated interior volume 115 of the conditioned space 103.

The controller 241 is provided with input communication channels that are arranged to receive information, data, or signals from, for example, the compressor 210, the power source 211, the condenser fan 224, the first valve 251, the evaporator fan 233, the second valve 252, a pressure sensor 243, a compressor discharge pressure sensor 244 and the leak sensor 242. The controller 241 is provided with output communication channels that are arranged to provide commands, signals, or data to, for example, the compressor 210, the power source 211, the condenser fan 224, the first valve 251, the evaporator fan 233 and the second valve 252.

The controller 241 can be provided with at least one processor that is programmed to execute various operations including, but not limited to, a leak detection and/or leak mitigation strategy based on information, data, or signals provided via the input communication channels and output commands via the output communication channels.

The leak sensor 242 is arranged to provide a signal indicative of a concentration, amount or the presence of refrigerant within the refrigerated interior volume 115 of the conditioned space 103 to the controller 241. The leak sensor 242 may be disposed proximate to the evaporator 230 and/or may be disposed proximate the refrigerant line 250 or any other refrigerant line or component that could leak refrigerant into the conditioned space 103. The leak sensor 242 may also be located near a likely location where refrigerant may collect, such as near the bottom wall 111.

While the refrigeration system 104 has been described in accordance with embodiments herein, it is to be understood that other embodiments of the refrigeration system 104 and that other conditioning systems exist and that the following description is relevant to each of these various embodiments and systems.

Figure 3:
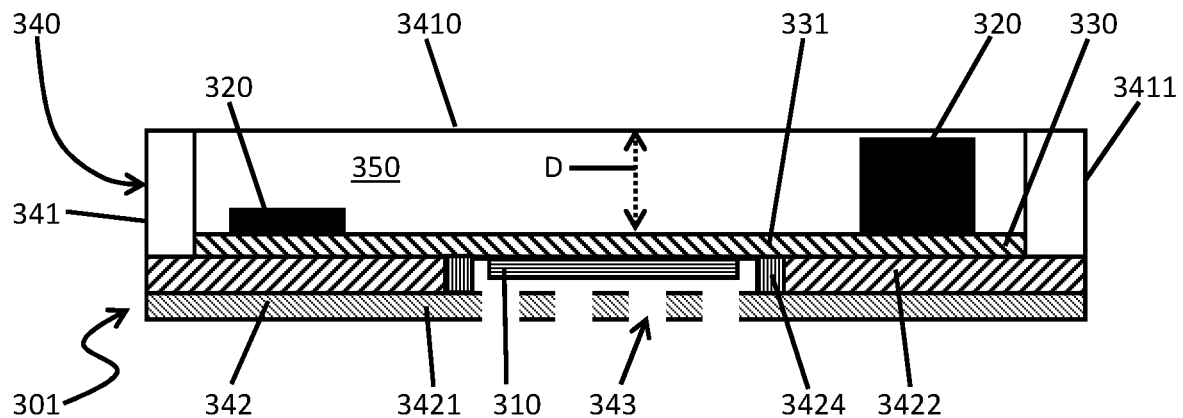
FIG. 3 is a side view of a gas detector in accordance with embodiments.
Figure 4:
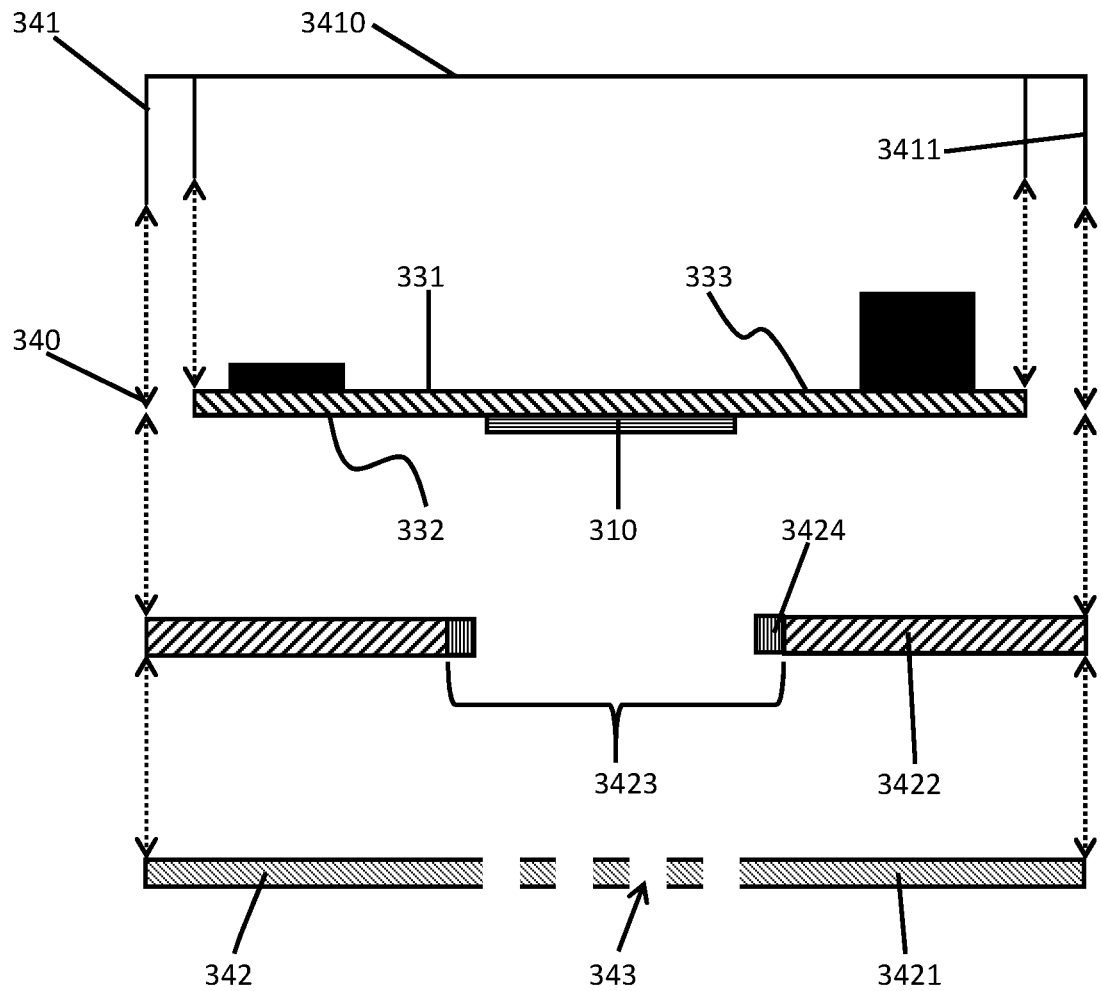
FIG. 4 is an exploded side view of the gas detector of FIG. 3.

With reference to FIGS. 3 and 4, a gas detector 301 can be provided as the leak sensor 242 of FIG. 2. The gas detector 301 includes a gas detector element 310 and gas detector electronics 320 to interface with the gas detector element 310. The gas detector electronics 320 can be communicative with the gas detector element 310 and, in some cases, can be configured to receive a signal from the gas detector element 310 and to process that signal into usable data that the gas detector electronics 320 can monitor and take action to address in an event the signal from the gas detector element 310 is above a threshold for safety. In still other cases, the gas detector electronics 320 can be configured to control certain operations of the gas detector element 310. In any case, the gas detector electronics 320 can be configured to communicate with the controller 241. The gas detector 301 can further include a printed circuit board (PCB) 330 on which the gas detector element 310 and the gas detector electronics 320 are disposable and an enclosure 340. The enclosure 340 is configured to expose the gas detector element 310 to an exterior (i.e., to the refrigerated interior volume 115, any gases or fluids therein and, in particular, to any leaked refrigerant therein). The enclosure 340 is further configured to cooperate with the PCB 330 to form an electronics housing area 350. The gas detector electronics 320 are disposable in the electronics housing area 350 whereby the gas detector electronics 320 are isolated from the exterior.

As shown in FIGS. 3 and 4, the PCB 330 includes a solid, unitary body 331, which is configured to impede fluid flow from the exterior, through the enclosure 340 and into the electronics housing area 350. The PCB 330 further includes a first side 332 and a second side 333 (see FIG. 4). The gas detector element 310 is disposable on the first side 332. The second side 333 is opposite the first side 332. The gas detector electronics 320 are disposable on the second side 333.

The enclosure 340 includes a body 341 and a cover 342. The PCB 330 is affixable to the body 341 and the cover 342 is affixable to the body 341 over the PCB 330 such that the PCB 330 is substantially surrounded by the body 341 and the cover 342 with the first side 332 of the PCB 330 facing the cover 342 and the second side 333 of the PCB 330 facing the body 341. The cover 342 is formed to define an aperture 343 through which the gas detector element 310 is exposed to the exterior and which may or may not have ribs or holes extending across open space. The body 341 is formed to define, in cooperation with the PCB 330, the electronics housing area 350 in which the gas detector electronics 320 are disposable.

In accordance with embodiments, the body 341 includes a back-plane 3410 that faces the second side 333 of the PCB 330 and sidewalls 3411 that are connected to the second side 333 of the PCB 330 and position the back-plane 3410 at a distance D from the second side 333 of the PCB 330. The electronics housing area 350 is thus delimited by the back-plane 3410, the sidewalls 3411 and the PCB 330. The distance D is sufficient to at least tightly accommodate the gas detector electronics 320.

The cover 342 includes a cover portion 3421 and a spacer portion 3422, which can be separate components or integrally provided together in a single component, and which is interposed between the first side 332 of the PCB 330 and the cover portion 3421. The spacer portion 3422 is thicker than the gas detector element 310, is formed to define an opening 3423 (see FIG. 4) to accommodate the gas detector element 310 and can, in some cases, include a seal 3424 at the opening 3423. The opening 3423 is large enough to form a space around the gas detector element 310 with or without the seal 3424 being present.

Figure 5:
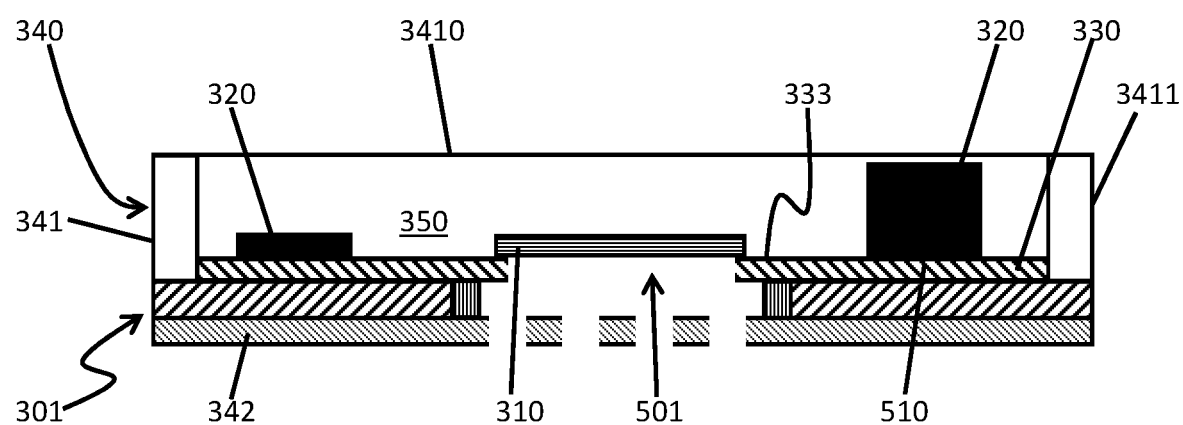
FIG. 5 is a side view of a gas detector in accordance with alternative embodiments.

In accordance with alternative embodiments and, with reference to FIG. 5, the gas detector element 310 and the gas detector electronics 320 are disposable on a same side (i.e., the second side 333) of the PCB 333. In these or other cases, the PCB 330 defines a PCB aperture 501 through which the gas detector element 310 is exposable to the exterior and the PCB 330 includes a solid, unitary body 510 surrounding the PCB aperture 501. Here, while the gas detector element 310 is exposed to the exterior through the PCB aperture 501, the connection or interface between the gas detector element 310 and the PCB 330 is sealed or otherwise impermeable such that the electronics housing area 350 is isolated from the exterior. In addition, the solid, unitary body 510 surrounding the PCB aperture 501 is configured to impede fluid flow from the exterior to the electronics housing area 350 which does not run through the PCB aperture 501.

Technical effects and benefits of the enclosure design of the present disclosure are reduced response times (e.g., from about 20 minutes to 1 minute) and protection of electrical systems from exposure to environmental effects like humidity, dust and other factors that can reduce reliability. The enclosure design will allow safety procedures to be initiated as quickly as possible in comparison to other designs. In addition, the configuration of the enclosure 340 is such that areas within the electronics housing area 350, in which gas can get trapped in conventional detectors, are isolated from the exterior of the enclosure 340 and minimized in terms of size and interior volume. As such, very little to no amount of gases or other atmospheric features (i.e., air, moisture, debris, etc.), which could adversely affect sensor readings, can become trapped in the electronics housing area 350.

While the disclosure is provided in detail in connection with only a limited number of embodiments, it should be readily understood that the disclosure is not limited to such disclosed embodiments. Rather, the disclosure can be modified to incorporate any number of variations, alterations, substitutions or equivalent arrangements not heretofore described, but which are commensurate with the spirit and scope of the disclosure. Additionally, while various embodiments of the disclosure have been described, it is to be understood that the exemplary embodiment(s) may include only some of the described exemplary aspects. Accordingly, the disclosure is not to be seen as limited by the foregoing description, but is only limited by the scope of the appended claims.

What is claimed is:

1. A gas detector for detecting refrigerant leakage in a space of a trailer, truck or cargo container, the gas detector comprising:
    a printed circuit board (PCB) on which a gas detector element and electronics to interface with the gas detector element are disposed, the gas detector element configured to detect the refrigerant leakage,
    wherein the PCB comprises a first side on which the gas detector element is disposable and a second side facing in an opposite direction from the first side and on which the electronics are disposable; and
    an enclosure comprising a body and a cover which are attachable together to substantially surround the PCB,
    the cover comprising a cover portion and a spacer portion interposed between the first side of the PCB and a corresponding side of the cover portion, wherein the spacer portion defines an opening to accommodate the gas detector element and the cover defines an aperture through which the gas detector element is exposed to an exterior of the enclosure and the refrigerant leakage via the opening of the spacer portion, and
    the body defining, in cooperation with the PCB, an electronics housing area in which the electronics are disposed, the electronics housing area being isolated from the exterior of the enclosure and the refrigerant leakage.

2. The gas detector according to claim 1, wherein the PCB comprises a solid, unitary body configured to impede fluid flow from the exterior of the enclosure to the electronics housing area.

3. The gas detector according to claim 1, wherein the PCB is affixable to the body and the cover is affixable to the body over the PCB.

4. The gas detector according to claim 1,
    wherein the spacer portion is thicker than the gas detector element and comprises a seal at the opening.

5. A gas detector for detecting refrigerant leakage in a space of a trailer, truck or cargo container, the gas detector comprising:
    a printed circuit board (PCB) defining a PCB aperture on which a gas detector element and electronics to interface with the gas detector element are disposed, the gas detector element configured to detect the refrigerant leakage via the PCB aperture; and
    an enclosure comprising a body and a cover which are attachable together to substantially surround the PCB,
    the cover comprising a cover portion and a spacer portion interposed between the PCB and the cover portion, wherein the spacer portion defines an opening at the PCB aperture to accommodate the gas detector element and the cover defines an aperture through which the gas detector element is exposed to an exterior of the enclosure and the refrigerant leakage via the PCB aperture and the opening of the spacer portion, and
    the body defining, in cooperation with the PCB, an electronics housing area in which the electronics are disposed, the electronics housing area being isolated from the exterior of the enclosure and the refrigerant leakage.

6. The gas detector according to claim 5, wherein the PCB comprises a solid, unitary body configured to impede fluid flow from the exterior of the enclosure to the electronics housing area.

7. The gas detector according to claim 5, wherein the PCB is affixable to the body and the cover is affixable to the body over the PCB.

8. The gas detector according to claim 5,
wherein the spacer portion is thicker than the gas detector element and comprises a seal at the opening.

* * * * *